(12) United States Patent
Trollsas et al.

(10) Patent No.: US 8,128,983 B2
(45) Date of Patent: Mar. 6, 2012

(54) COATING COMPRISING POLY(ETHYLENE GLYCOL)-POLY(LACTIDE-GLYCOLIDE-CAPROLACTONE) INTERPENETRATING NETWORK

(75) Inventors: Mikael Trollsas, San Jose, CA (US);
Florencia Lim, Union City, CA (US);
Syed F. A. Hossainy, Fremont, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 12/101,866

(22) Filed: Apr. 11, 2008

(65) Prior Publication Data
US 2009/0259302 A1    Oct. 15, 2009

(51) Int. Cl.
*A61L 33/00* (2006.01)

(52) U.S. Cl. ............... 427/2.24; 623/17.11; 623/1.42; 623/17.16; 623/926; 623/23.58; 525/453; 424/426; 427/2.25; 427/430.1; 427/435; 427/443.2

(58) Field of Classification Search .............. 623/1.42, 623/17.11, 23.75, 17.16, 926, 23.58; 525/453; 424/426
See application file for complete search history.

(56) References Cited

U.S. PATENT DOCUMENTS

| | | | |
|---|---|---|---|
| 4,733,665 A | 3/1988 | Palmaz | |
| 4,800,882 A | 1/1989 | Gianturco | |
| 4,886,062 A | 12/1989 | Wiktor | |
| 5,272,012 A | 12/1993 | Opolski | |
| 5,702,754 A | 12/1997 | Zhong | |
| 5,863,650 A | 1/1999 | Healy et al. | |
| 5,997,517 A | 12/1999 | Whitbourne | |
| 6,001,117 A | 12/1999 | Huxel et al. | |
| 6,110,483 A | 8/2000 | Whitbourne et al. | |
| 6,224,893 B1 | 5/2001 | Langer et al. | |
| 6,274,164 B1 | 8/2001 | Novich | |
| 6,306,176 B1 | 10/2001 | Whitbourne | |
| 6,451,346 B1 | 9/2002 | Shah et al. | |
| 6,494,862 B1 | 12/2002 | Ray et al. | |
| 6,495,127 B1 | 12/2002 | Wallace et al. | |
| 6,503,538 B1 | 1/2003 | Chu et al. | |
| 6,544,223 B1 | 4/2003 | Kokish | |
| 6,544,543 B1 | 4/2003 | Buchk et al. | |
| 6,656,216 B1 | 12/2003 | Hossainy | |
| 6,656,506 B1 | 12/2003 | Wu et al. | |
| 6,663,662 B2 | 12/2003 | Pacetti et al. | |

(Continued)

FOREIGN PATENT DOCUMENTS

WO    WO 2005/000939    1/2005

OTHER PUBLICATIONS

Chen et al., Redifferentiation of dedifferentiated bovinechondrocytes when cultured in vitro in a PLGA-collagen hybrid mesh, Apr. 14, 2003, FEBS Letters 542, pp. 95-99.*

(Continued)

*Primary Examiner* — Dah-Wei Yuan
*Assistant Examiner* — Andrew Bowman
(74) *Attorney, Agent, or Firm* — Squire Sanders (US) LLP

(57) ABSTRACT

Methods for fabricating coatings for implantable medical devices are disclosed. The method comprises forming a coating on an implantable device comprising an interpenetrating network or semi-interpenetrating network. The interpenetrating network or semi-interpenetrating network comprises poly(ethylene glycol) and an aliphatic polyester copolymer. It is also provided an implantable device and a method of using the implantable device.

15 Claims, 4 Drawing Sheets

U.S. PATENT DOCUMENTS

| | | |
|---|---|---|
| 6,663,880 B1 | 12/2003 | Roorda et al. |
| 6,673,154 B1 | 1/2004 | Pacetti et al. |
| 6,703,040 B2 | 3/2004 | Katsarava |
| 6,712,845 B2 | 3/2004 | Hossainy |
| 6,743,462 B1 | 6/2004 | Pacetti |
| 6,753,071 B1 | 6/2004 | Pacetti |
| 6,758,859 B1 | 7/2004 | Kenny |
| 6,790,228 B2 | 9/2004 | Hossainy |
| 6,818,063 B1 | 11/2004 | Kerrigan |
| 6,824,559 B2 | 11/2004 | Michal |
| 6,896,965 B1 | 5/2005 | Hossainy |
| 6,926,919 B1 | 8/2005 | Hossainy et al. |
| 6,972,054 B2 | 12/2005 | Kerrigan |
| 7,005,137 B1 | 2/2006 | Hossainy et al. |
| 7,022,334 B1 | 4/2006 | Ding |
| 7,056,591 B1 | 6/2006 | Pacetti et al. |
| 7,060,093 B2 | 6/2006 | Dang |
| 7,063,884 B2 | 6/2006 | Hossainy et al. |
| 7,074,276 B1 | 7/2006 | Van Sciver et al. |
| 7,115,300 B1 | 10/2006 | Hossainy et al. |
| 7,135,038 B1 | 11/2006 | Limon |
| 7,166,680 B2 | 1/2007 | Desnoyer |
| 7,169,178 B1 | 1/2007 | Santos et al. |
| 7,175,874 B1 | 2/2007 | Pacetti |
| 7,201,935 B1 | 4/2007 | Claude et al. |
| 7,202,325 B2 | 4/2007 | Hossainy |
| 7,217,426 B1 | 5/2007 | Hossainy |
| 7,232,490 B1 | 6/2007 | Hossainy |
| 7,232,573 B1 | 6/2007 | Ding |
| 7,244,443 B2 | 7/2007 | Pacetti |
| 7,247,313 B2 | 7/2007 | Roorda et al. |
| 7,247,364 B2 | 7/2007 | Hossainy et al. |
| 7,255,891 B1 | 8/2007 | Pacetti |
| 7,261,946 B2 | 8/2007 | Claude |
| 7,288,609 B1 | 10/2007 | Pacetti |
| 7,294,329 B1 | 11/2007 | Ding |
| 7,311,980 B1 | 12/2007 | Hossainy et al. |
| 7,323,209 B1 | 1/2008 | Esbeck et al. |
| 7,329,413 B1 | 2/2008 | Pacetti |
| 7,335,265 B1 | 2/2008 | Hossainy |
| 7,335,391 B1 | 2/2008 | Pacetti |
| 7,341,630 B1 | 3/2008 | Pacetti |
| 7,354,480 B1 | 4/2008 | Kokish et al. |
| 7,390,524 B1 | 6/2008 | Chen |
| 7,396,539 B1 | 7/2008 | Hossainy et al. |
| 7,431,959 B1 | 10/2008 | Dehnad |
| 2001/0007083 A1 | 7/2001 | Roorda |
| 2001/0008980 A1* | 7/2001 | Gresser et al. ............. 623/17.11 |
| 2003/0073961 A1 | 4/2003 | Happ |
| 2003/0104028 A1 | 6/2003 | Hossainy et al. |
| 2003/0105518 A1 | 6/2003 | Dutta |
| 2003/0158517 A1 | 8/2003 | Kokish |
| 2003/0082368 A1 | 10/2003 | Hossainy |
| 2004/0024143 A1* | 2/2004 | Lendlein et al. ............. 525/453 |
| 2004/0047980 A1 | 3/2004 | Pacetti |
| 2004/0052858 A1 | 3/2004 | Wu et al. |
| 2004/0054104 A1 | 3/2004 | Pacetti |
| 2004/0060508 A1 | 4/2004 | Pacetti |
| 2004/0062853 A1 | 4/2004 | Pacetti et al. |
| 2004/0063805 A1 | 4/2004 | Hossainy |
| 2004/0071861 A1 | 4/2004 | Mandrusov |
| 2004/0072922 A1 | 4/2004 | Hossainy |
| 2004/0073298 A1 | 4/2004 | Hossainy |
| 2004/0086542 A1 | 5/2004 | Hossainy |
| 2004/0106987 A1* | 6/2004 | Palasis et al. ............. 623/1.42 |
| 2004/0142015 A1 | 7/2004 | Hossainy et al. |
| 2004/0162609 A1 | 8/2004 | Hossainy et al. |
| 2004/0180132 A1 | 9/2004 | Pacetti |
| 2004/0182312 A1 | 9/2004 | Pacetti et al. |
| 2004/0191405 A1 | 9/2004 | Kerrigan |
| 2004/0224001 A1 | 11/2004 | Pacetti et al. |
| 2004/0253203 A1 | 12/2004 | Hossainy |
| 2005/0021127 A1 | 1/2005 | Kawula |
| 2005/0025799 A1 | 2/2005 | Hossainy |
| 2005/0031669 A1* | 2/2005 | Shafiee et al. ............. 424/426 |
| 2005/0074544 A1 | 4/2005 | Pacetti et al. |
| 2005/0112170 A1 | 5/2005 | Hossainy et al. |
| 2005/0112171 A1 | 5/2005 | Tang et al. |
| 2005/0118344 A1 | 6/2005 | Pacetti |
| 2005/0137381 A1 | 6/2005 | Pacetti |
| 2005/0147647 A1 | 7/2005 | Glauser et al. |
| 2005/0169957 A1 | 8/2005 | Hossainy |
| 2005/0175666 A1 | 8/2005 | Ding |
| 2005/0208091 A1 | 9/2005 | Pacetti |
| 2005/0214339 A1 | 9/2005 | Tang et al. |
| 2005/0226991 A1 | 10/2005 | Hossainy et al. |
| 2005/0244363 A1 | 11/2005 | Hossainy et al. |
| 2005/0265960 A1 | 12/2005 | Pacetti et al. |
| 2005/0271700 A1 | 12/2005 | Desnoyer et al. |
| 2005/0287184 A1 | 12/2005 | Hossainy et al. |
| 2006/0002968 A1 | 1/2006 | Stewart et al. |
| 2006/0034888 A1 | 2/2006 | Pacetti et al. |
| 2006/0043650 A1 | 3/2006 | Hossainy et al. |
| 2006/0062824 A1 | 3/2006 | Pacetti et al. |
| 2006/0089485 A1 | 4/2006 | Desnoyer et al. |
| 2006/0095122 A1 | 5/2006 | Pacetti |
| 2006/0115449 A1 | 6/2006 | Pacetti |
| 2006/0134165 A1 | 6/2006 | Pacetti |
| 2006/0136048 A1 | 6/2006 | Pacetti et al. |
| 2006/0160985 A1 | 7/2006 | Pacetti et al. |
| 2007/0322853 | 2/2007 | Hossainy et al. |

OTHER PUBLICATIONS

U.S. Appl. No. 09/406,473, filed Sep. 27, 1999, Pacetti.
U.S. Appl. No. 10/040,538, filed Dec. 28, 2001, Pacetti et al.
U.S. Appl. No. 10/177,942, filed Jun. 21, 2002, Michal et al.
U.S. Appl. No. 10/316,739, filed Dec. 10, 2002, Zhang et al.
U.S. Appl. No. 10/330,412, filed Dec. 27, 2002, Hossainy et al.
U.S. Appl. No. 10/375,496, filed Feb. 26, 2003, Esbeck.
U.S. Appl. No. 10/376,348, filed Feb. 26, 2003, Ding et al.
U.S. Appl. No. 10/428,691, filed May 1, 2003, Pacetti.
U.S. Appl. No. 10/606,711, filed Jun. 26, 2003, Pacetti.
U.S. Appl. No. 10/705,546, filed Nov. 10, 2003, Kwok et al.
U.S. Appl. No. 10/835,229, filed Apr. 28, 2004, Prabhu et al.
U.S. Appl. No. 10/853,924, filed May 25, 2004, Pathak.
U.S. Appl. No. 10/877,419, filed Jun. 25, 2004, Pacetti.
U.S. Appl. No. 10/883,242, filed Jun. 30, 2004, Roorda et al.
U.S. Appl. No. 10/909,795, filed Jul. 30, 2004, Ding et al.
U.S. Appl. No. 10/913,607, filed Aug. 5, 2004, Pacetti et al.
U.S. Appl. No. 10/976,550, filed Oct. 29, 2004, Pacetti et al.
Design of Biopharmaceutical Properties through Prodrugs and Analogs, Editor Edward B. Roche, Book, 4 title pages (1977).
Martin et al., "Enhancing the biological activity of immobilized osteopontin using a type-1 collagen affinity coating", Wiley Periodicals, Inc., pp. 10-19 (2004).
Norman J. Harper, "Drug Latentiation", Progress in Drug Research, pp. 221-294 (1962).
Sinkula et al., "Rational for Design of Biological Reversible Drug Derivatives: Prodrugs", Journal of Pharmaceutical Sciences, Vo. 64, No. 2, pp. 181-210 (1975).
Spagnuolo et al., "Gas 1 is induced by VE-cadherin and vascular endothelial growth factor and inhibits endothelial cell apoptosis", Blood, vol. 103, No. 8, pp. 3005-3012 (2004).
Stella et el., "Prodrugs: Do they Have Advanteges in Clinical Practice?", Drugs, vol. 29, pp. 455-473 (1985).
Volkel et al., "Targeting of immunolipsomes to Endothelial cells using a single-chain Fv fragment directed against human endoglin (CD105)", Biochimica et Biophysica Acta, vol. 1663, pp. 158-166 (2004).
International Search Report for PCT/US2009/039691, mailed Jun. 22, 2010, 12 pgs.

* cited by examiner

COATING COMPRISING POLY(ETHYLENE GLYCOL)-POLY(LACTIDE-GLYCOLIDE-CAPROLACTONE) INTERPENETRATING NETWORK

BACKGROUND OF THE INVENTION

1. Field of the Invention

This invention is directed to coatings for drug delivery devices, such as drug delivery vascular stents, and methods for making and using the same.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

Local administration of therapeutic agents via stents has shown some favorable results in reducing restenosis. However, the properties of stent coatings can be improved. For example, in a drug delivery coating of polylactic acid or poly(lactic acid-co-glycolic acid), phase separation of the drug and polymers has been observed, which can lead to undesirable level of control of the release of drug. Therefore, there is a need for materials that provide a better way for controlling drug release and improving coating integrity post high temperature processing such as EtO sterilization and stent crimping.

Embodiments of the present invention described below address the above identified issues and needs.

SUMMARY

In according to an aspect of the present invention, it is provided a method for fabricating a coating for an implantable medical device. The method comprises forming a coating on the device, the coating comprising an interpenetrating network (IPN) or semi-IPN, wherein the IPN or semi-IPN comprises poly(ethylene glycol) (PEG) and an aliphatic polyester copolymer. The coating can be formed by various methods. In some embodiments, forming a coating comprises crosslinking the PEG and/or the aliphatic polyester copolymer. In some other embodiments, forming a coating comprises crosslinking the PEG and/or the aliphatic polyester copolymer with a bifunctional or multifunctional crosslinking agent. In some embodiments, the aliphatic polyester copolymer can comprise an electronic unsaturation, and forming a coating comprises crosslinking the aliphatic polyester copolymer.

In some embodiments, the aliphatic polyester copolymer can comprise D,L-lactide or L-lactide. In some embodiments, the aliphatic polyester copolymer can comprise glycolide (GA). In some embodiments, the aliphatic polyester copolymer can comprise poly(L-lactide-co-glycolide-co-caprolactone) (PLGACL) or poly(D,L-lactide-co-glycolide-co-caprolactone) (PDLA-GA-CL), poly(lactide-co-glycolide) (PLGA), or poly(butylene succinate). Where the IPN or semi-IPN comprises both lactide and glycolide, the lactide and glycolide can have different molar ratios, e.g., a molar ratio of lactide to glycolide ranging from about 50% to about 90% such as 75:25.

The IPN or semi-IPN can comprise various levels of PEG. In some embodiments, the IPN or semi-IPN comprises from about 1% to about 40% PEG by mass of the IPN or semi-IPN. In some embodiments, the IPN or semi-IPN comprises from about 2% to about 25% PEG by mass of the IPN or semi-IPN. In some further embodiments, the IPN or semi-IPN comprises from about 2% to about 10% PEG by mass of the IPN or semi-IPN.

The coating can further include a bioactive agent such as a drug. The bioactive agent and the IPN or semi-IPN can have different drug:polymer (D:P) ratio by weight. Examples of such ratios of the bioactive agent to the IPN or semi-IPN can be from about 1:1 to about 1:5. Examples of the bioactive agent are paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, dexamethasone acetate, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), zotarolimus, Biolimus A9 (Biosensors International, Singapore), AP23572 (Ariad Pharmaceuticals), γ-hiridun, clobetasol, pimecrolimus, imatinib mesylate, midostaurin, feno fibrate, prodrugs thereof, co-drugs thereof, or combinations thereof.

The implantable device can be any implantable device. An example of the implantable device is a stent or a bioabsorbable stent.

In according to another aspect of the present invention, it is provided an implantable medical device comprising a coating. Embodiments of the coating are as described above.

In according to another aspect of the present invention, it is provided a method, the method comprises implanting an implantable device. Embodiments of the implantable device are as described above.

DETAILED DESCRIPTION

Figure 1A:
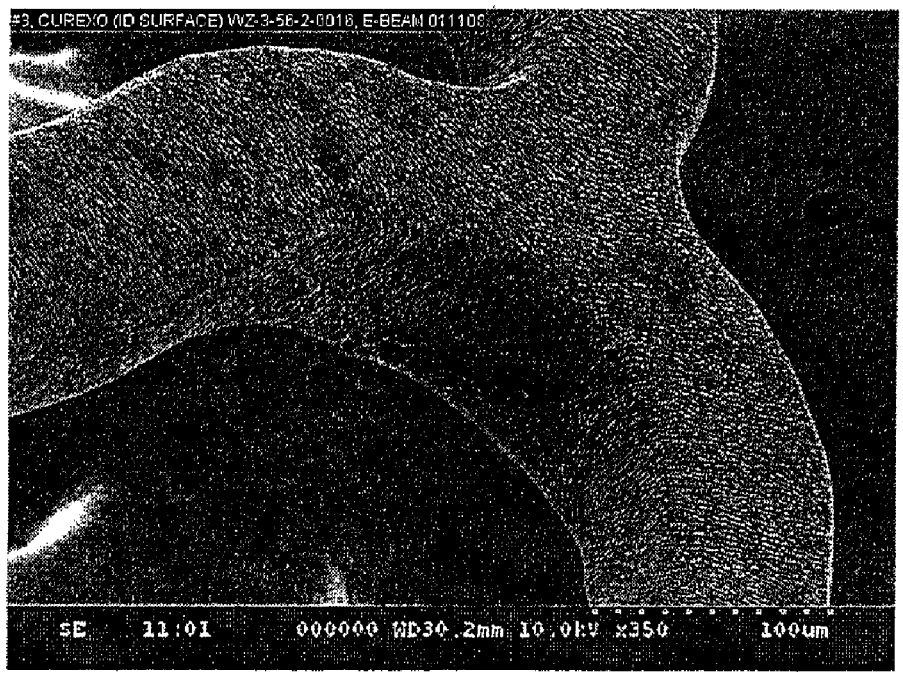
FIGS. 1A-1F show scanning electronic microscope (SEM) images of coatings formed of poly(ethylene glycol)-poly(lactide-co-glycolide) interpenetrating network.

In accordance with an aspect of the present invention, it is provided a coating on an implantable device. The coating includes a bioactive agent and an interpenetrating network (IPN) or a semi-IPN comprising polyethylene glycol (PEG) and at least one aliphatic polyester. The IPN or semi-IPN will entrap the drug and minimize bulk erosion of the polymer matrix and therefore provides zero order release of the drug by controlled erosion.

In some embodiments, the IPN or semi-IPN is poly(lactide-co-glycolide-co-caprolactone) (PLGACL) (PEG/PLGACL-IPN) or a semi-interpenetrating network of PEG and PLGACL (PEG/PLGACL-semi-IPN). A coating formed of such an IPN or semi-IPN can have tunable drug release or coating properties. For example, by varying the ratio of PEG and PLGACL as well the ratios of lactide to glycolide and caprolactone in the polymer system, the rate and duration of drug release can be controlled. In addition, varying composition of the PEG and PLGA can be tailored to impart elasticity to the coating for achieving good integrity of the coating and to control degradation of the coating material. Lactide units in the IPN or semi-IPN also cause the coating to be more robust for high temperature processing such as EtO sterilization and stent crimping. (SEE GRAPH ON RELEASE RATE FOR THREE DIFFERENT IPN SAMPLES).

In some embodiments, the IPN or semi-IPN can be constructed using PEG-co-poly(butylene succinate) and PLGA or constructed using PEG-co-PLGA with PLGA.

The IPN or semi-IPN described herein can have different concentration of PEG. PEG is a hydrophilic and non-fouling polymer. PEG in the IPN or semi-IPN thus will impart a degree of hydrophilicity and non-fouling property that is directly related to the content of PEG in the IPN or semi-IPN. Generally, an IPN or semi-IPN can have about a PEG content from about % to 40% by mass, preferably about 2% to about 25% by mass, and most preferably about 2% to about 10% by mass, of the total weight of the IPN or semi-IPN.

The polyester polymer imparts hydrophobicity, mechanical strength, elasticity to an IPN or semi-IPN. Polyester polymers have different rate of degradation. Generally, as compared to lactide, glycolide imparts a relatively faster rate of degradation to the polyester. An IPN or semi-IPN having a higher content of glycolide generally degrades faster while an IPN or semi-IPN having a higher content of lactide is generally more elastic. Therefore, when an IPN or semi-IPN includes both glycolide and lactide, the molar ratio of lactide to glycolide can be from about 50% to about 90%. The lactide can be racemic-lactide, a mixture of D-lactide and L-lactide or L-lactide or D-Lactide.

The IPN or semi-IPN can be included in a layer of coating on an implantable device alone or with a bioactive agent as a drug delivery matrix or drug reservoir layer. In some embodiments, a coating including the IPN or semi-IPN described herein can include an amorphous primer layer so as to improve adhesion of the coating to the surface of implantable device having the coating. In some embodiments, the amorphous primer layer can be bioabsorbable or non-absorbable. In some embodiments, the primer layer can be formed of poly(D,L-lactide-co-glycolide) (PDLGA) with a molar ratio of lactide to glycolide of about 75:25.

As used herein, the term IPN refers to a polymer network comprising two or more polymers which are at least partially interlaced on a molecular scale but not covalently bonded to each other and cannot be separated unless chemical bonds are broken. Generally, the three conditions for eligibility as an IPN are: (1) the two polymers are synthesized and/or crosslinked in the presence of the other, (2) the two polymers have similar kinetics, and (3) the two polymers are not dramatically phase separated. The term "semi-IPN" refers to a polymer network of two or more polymers wherein at least one polymer is crosslinked and at least one polymer is uncrosslinked.

Formation of an IPN or semi-IPN can be achieved by well documented methods. Generally, forming an IPN involves crosslinking of polymers in the IPN construct via crosslinking of the functional groups in the polymers with or without a crosslinking agent. For example, crosslinking between polymer chains can happen using a bi-functional or multifunctional crosslinking agent or linking agent. The crosslinking agent will cause polymers to crosslink, thereby forming the IPN or semi-IPN. In some embodiments, crosslinking can occur by curing of a coating at an elevated temperature comprising curable polymers. An elevated temperature, as used herein, refers to a temperature higher than the ambient temperature.

Linking agents useful for forming an IPN or semi-IPN described here can be any molecules having two or more functional groups. Such functional groups include, but are not limited to, hydroxyl, thiol, carboxylic acid, sulfonic acid, sulfate, phosphonic acid, phosphate, amino, aldehydes, isocyanate, compounds with two unsaturated groups such as diacrylate, dimethacrylate or compounds with two vinyl groups or two allyl groups. Exemplary linking agents include, but are not limited to, glutaraldehyde, N,N'-methylenebisacrylamide (BisAAM), etc.

DEFINITIONS

Wherever applicable, the definitions to some terms used throughout the description of the present invention as provided below shall apply.

The terms "biologically degradable" (or "biodegradable"), "biologically erodable" (or "bioerodable"), "biologically absorbable" (or "bioabsorbable"), and "biologically resorbable" (or "bioresorbable"), in reference to polymers and coatings, are used interchangeably and refer to polymers and coatings that are capable of being completely or substantially completely degraded, dissolved, and/or eroded over time when exposed to physiological conditions and can be gradually resorbed, absorbed and/or eliminated by the body, or that can be degraded into fragments that can pass through the kidney membrane of an animal (e.g., a human), e.g., fragments having a molecular weight of about 40,000 Daltons (40 kDa) or less. The process of breaking down and eventual absorption and elimination of the polymer or coating can be caused by, e.g., hydrolysis, metabolic processes, oxidation, enzymatic processes, bulk or surface erosion, and the like. Conversely, a "biostable" polymer or coating refers to a polymer or coating that is not biodegradable.

Whenever the reference is made to "biologically degradable," "biologically erodable," "biologically absorbable," and "biologically resorbable" stent coatings or polymers forming such stent coatings, it is understood that after the process of degradation, erosion, absorption, and/or resorption has been completed or substantially completed, no coating or substantially little coating will remain on the stent. Whenever the terms "degradable," "biodegradable," or "biologically degradable" are used in this application, they are intended to broadly include biologically degradable, biologically erodable, biologically absorbable, and biologically resorbable polymers or coatings.

"Physiological conditions" refer to conditions to which an implant is exposed within the body of an animal (e.g., a human). Physiological conditions include, but are not limited to, "normal" body temperature for that species of animal (approximately 37° C. for a human) and an aqueous environment of physiologic ionic strength, pH and enzymes. In some cases, the body temperature of a particular animal may be above or below what would be considered "normal" body temperature for that species of animal. For example, the body temperature of a human may be above or below approximately 37° C. in certain cases. The scope of the present invention encompasses such cases where the physiological conditions (e.g., body temperature) of an animal are not considered "normal." In the context of a blood-contacting implantable device, a "prohealing" drug or agent refers to a drug or agent that has the property that it promotes or enhances re-endothelialization of arterial lumen to promote healing of the vascular tissue.

As used herein, a "co-drug" is a drug that is administered concurrently or sequentially with another drug to achieve a particular pharmacological effect. The effect may be general or specific. The co-drug may exert an effect different from that of the other drug, or it may promote, enhance or potentiate the effect of the other drug.

As used herein, the term "prodrug" refers to an agent rendered less active by a chemical or biological moiety, which metabolizes into or undergoes in vivo hydrolysis to form a drug or an active ingredient thereof. The term "prodrug" can be used interchangeably with terms such as "proagent", "latentiated drugs", "bioreversible derivatives", and "congeners". N.J. Harper, Drug latentiation, *Prog Drug Res.,* 4: 221-294 (1962); E. B. Roche, Design of Biopharmaceutical Properties through Prodrugs and Analogs, Washington, D.C.: American Pharmaceutical Association (1977); A. A. Sinkula and S. H. Yalkowsky, Rationale for design of biologically reversible drug derivatives: prodrugs, *J. Pharm. Sci.,* 64: 181-210 (1975). Use of the term "prodrug" usually implies a covalent link between a drug and a chemical moiety, though some authors also use it to characterize some forms of salts of the active drug molecule. Although there is no strict universal definition of a prodrug itself, and the definition may vary from author to author, prodrugs can generally be defined as pharmacologically less active chemical derivatives that can be converted in vivo, enzymatically or nonenzymatically, to the active, or more active, drug molecules that exert a therapeutic, prophylactic or diagnostic effect. Sinkula and Yalkowsky, above; V. J. Stella et al., Prodrugs: Do they have advantages in clinical practice?, *Drugs,* 29: 455-473 (1985).

The terms "polymer" and "polymeric" refer to compounds that are the product of a polymerization reaction. These terms are inclusive of homopolymers (i.e., polymers obtained by polymerizing one type of monomer by either chain or condensation polymers), copolymers (i.e., polymers obtained by polymerizing two or more different types of monomers by either chain or condensation polymers), condensation polymers (polymers made from condensation polymerization, terpolymers, etc., including random (by either chain or condensation polymers), alternating (by either chain or condensation polymers), block (by either chain or condensation polymers), graft, dendritic, crosslinked and any other variations thereof.

As used herein, the term "implantable" refers to the attribute of being implantable in a mammal (e.g., a human being or patient) that meets the mechanical, physical, chemical, biological, and pharmacological requirements of a device provided by laws and regulations of a governmental agency (e.g., the U.S. FDA) such that the device is safe and effective for use as indicated by the device. As used herein, an "implantable device" may be any suitable substrate that can be implanted in a human or non-human animal. Examples of implantable devices include, but are not limited to, self-expandable stents, balloon-expandable stents, coronary stents, peripheral stents, stent-grafts, catheters, other expandable tubular devices for various bodily lumen or orifices, grafts, vascular grafts, arterio-venous grafts, by-pass grafts, pacemakers and defibrillators, leads and electrodes for the preceding, artificial heart valves, anastomotic clips, arterial closure devices, patent foramen ovale closure devices, cerebrospinal fluid shunts, and particles (e.g., drug-eluting particles, microparticles and nanoparticles). The stents may be intended for any vessel in the body, including neurological, carotid, vein graft, coronary, aortic, renal, iliac, femoral, popliteal vasculature, and urethral passages. An implantable device can be designed for the localized delivery of a therapeutic agent. A medicated implantable device may be constructed in part, e.g., by coating the device with a coating material containing a therapeutic agent. The body of the device may also contain a therapeutic agent.

An implantable device can be fabricated with a coating containing partially or completely a biodegradable/bioabsorbable/bioerodable polymer, a biostable polymer, or a combination thereof. An implantable device itself can also be fabricated partially or completely from a biodegradable/bioabsorbable/bioerodable polymer, a biostable polymer, or a combination thereof.

As used herein, a material that is described as a layer or a film (e.g., a coating) "disposed over" an indicated substrate (e.g., an implantable device) refers to, e.g., a coating of the material deposited directly or indirectly over at least a portion of the surface of the substrate. Direct depositing means that the coating is applied directly to the exposed surface of the substrate. Indirect depositing means that the coating is applied to an intervening layer that has been deposited directly or indirectly over the substrate. In some embodiments, the term a "layer" or a "film" excludes a film or a layer formed on a non-implantable device.

In the context of a stent, "delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

Generally, hydrophobicity of a polymer can be gauged using the Hildebrand solubility parameter, δ. The term "Hildebrand solubility parameter" refers to a parameter measuring the cohesion of a substance. The δ parameter is determined as follows:

$$\delta = (\Delta E/V)^{1/2}$$

where δ is the solubility parameter, $(cal/cm^3)^{1/2}$;
ΔE is the energy of vaporization, cal/mole; and
V is the molar volume, $cm^3$/mole.

Whichever polymer in the polymer blend has lower δ value compared to the δ value of the other polymer in the blend is designated as a hydrophobic polymer, and the polymer with higher δ value is designated as hydrophilic. If more than two polymers are used in the blend, then each can be ranked in order of its δ value. For the practice of the present invention, the value of δ of a particular polymer is inconsequential for classifying a polymer as hydrophobic or hydrophilic so long as the difference in the δ values of the two polymers is sufficient to allow the hydrophilic polymer to migrate or bloom to the surface as described below. In one exemplary embodiment, the δ value defining the boundary between the hydrophobic and hydrophilic components of the polymer blend can be about $11(cal/cm^3)^{1/2}$.

Biologically Active Agents

In some embodiments, the implantable device described herein can optionally include at least one biologically active ("bioactive") agent. The at least one bioactive agent can include any substance capable of exerting a therapeutic, prophylactic or diagnostic effect for a patient.

Examples of suitable bioactive agents include, but are not limited to, synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. The bioactive agents could be designed, e.g., to inhibit the activity of vascular smooth muscle cells. They could be directed at inhibiting abnormal or inappropriate migration and/or proliferation of smooth muscle cells to inhibit restenosis.

In certain embodiments, optionally in combination with one or more other embodiments described herein, the implantable device can include at least one biologically active agent selected from antiproliferative, antineoplastic, antimitotic, anti-inflammatory, antiplatelet, anticoagulant, antifibrin, antithrombin, antibiotic, antiallergic and antioxidant substances.

An antiproliferative agent can be a natural proteineous agent such as a cytotoxin or a synthetic molecule. Examples of antiproliferative substances include, but are not limited to, actinomycin D or derivatives and analogs thereof (manufactured by Sigma-Aldrich, or COSMEGEN available from Merck) (synonyms of actinomycin D include dactinomycin, actinomycin IV, actinomycin $I_1$, actinomycin $X_1$, and actinomycin $C_1$); all taxoids such as taxols, docetaxel, and paclitaxel and derivatives thereof; all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Examples of rapamycin derivatives include, but are not limited to, 40-O-(2-hydroxy)ethyl-rapamycin (trade name everolimus from Novartis), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus, manufactured by Abbott Labs.), prodrugs thereof, co-drugs thereof, and combinations thereof.

An anti-inflammatory drug can be a steroidal anti-inflammatory drug, a nonsteroidal anti-inflammatory drug (NSAID), or a combination thereof. Examples of anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

Alternatively, the anti-inflammatory agent can be a biological inhibitor of pro-inflammatory signaling molecules. Anti-inflammatory biological agents include antibodies to such biological inflammatory signaling molecules.

In addition, the bioactive agents can be other than antiproliferative or anti-inflammatory agents. The bioactive agents can be any agent that is a therapeutic, prophylactic or diagnostic agent. In some embodiments, such agents can be used in combination with antiproliferative or anti-inflammatory agents. These bioactive agents can also have antiproliferative and/or anti-inflammatory properties or can have other properties such as antineoplastic, antimitotic, cystostatic, antiplatelet, anticoagulant, antifibrin, antithrombin, antibiotic, antiallergic, and/or antioxidant properties.

Examples of antineoplastics and/or antimitotics include, but are not limited to, paclitaxel (e.g., TAXOL® available from Bristol-Myers Squibb), docetaxel (e.g., Taxotere® from Aventis), methotrexate, azathioprine, vincristine, vinblastine, fluorouracil, doxorubicin hydrochloride (e.g., Adriamycin® from Pfizer), and mitomycin (e.g., Mutamycin® from Bristol-Myers Squibb).

Examples of antiplatelet, anticoagulant, antifibrin, and antithrombin agents that can also have cytostatic or antiproliferative properties include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX™ (bivalirudin, from Biogen), calcium channel blockers (e.g., nifedipine), colchicine, fibroblast growth factor (FGF) antagonists, fish oil (e.g., omega 3-fatty acid), histamine antagonists, lovastatin (a cholesterol-lowering drug that inhibits HMG-CoA reductase, brand name Mevacor® from Merck), monoclonal antibodies (e.g., those specific for platelet-derived growth factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetics, 4-amino-2,2,6,6-tetramethylpiperidine-1-oxyl (4-amino-TEMPO), estradiol, anticancer agents, dietary supplements such as various vitamins, and a combination thereof.

Examples of cytostatic substances include, but are not limited to, angiopeptin, angiotensin converting enzyme inhibitors such as captopril (e.g., Capoten® and Capozide® from Bristol-Myers Squibb), cilazapril and lisinopril (e.g., Prinivil® and Prinzide® from Merck).

Examples of antiallergic agents include, but are not limited to, permirolast potassium. Examples of antioxidant substances include, but are not limited to, 4-amino-2,2,6,6-tetramethylpiperidine-1-oxyl (4-amino-TEMPO). Other bioactive agents include anti-infectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary vasodilators; peripheral and cerebral vasodilators; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Other biologically active agents that can be used include alpha-interferon, genetically engineered epithelial cells, tacrolimus and dexamethasone.

A "prohealing" drug or agent, in the context of a blood-contacting implantable device, refers to a drug or agent that has the property that it promotes or enhances re-endothelialization of arterial lumen to promote healing of the vascular tissue. The portion(s) of an implantable device (e.g., a stent) containing a prohealing drug or agent can attract, bind, and eventually become encapsulated by endothelial cells (e.g., endothelial progenitor cells). The attraction, binding, and encapsulation of the cells will reduce or prevent the formation of emboli or thrombi due to the loss of the mechanical properties that could occur if the stent was insufficiently encapsulated. The enhanced re-endothelialization can promote the endothelialization at a rate faster than the loss of mechanical properties of the stent.

The prohealing drug or agent can be dispersed in the body of the bioabsorbable polymer substrate or scaffolding. The prohealing drug or agent can also be dispersed within a bioabsorbable polymer coating over a surface of an implantable device (e.g., a stent).

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

In some embodiments, the prohealing drug or agent can be an endothelial cell (EDC)-binding agent. In certain embodiments, the EDC-binding agent can be a protein, peptide or antibody, which can be, e.g., one of collagen type 1, a 23 peptide fragment known as single chain Fv fragment (scFv A5), a junction membrane protein vascular endothelial (VE)-cadherin, and combinations thereof. Collagen type 1, when bound to osteopontin, has been shown to promote adhesion of endothelial cells and modulate their viability by the down regulation of apoptotic pathways. S. M. Martin, et al., *J. Biomed. Mater. Res.*, 70A:10-19 (2004). Endothelial cells can be selectively targeted (for the targeted delivery of immunoliposomes) using scFv A5. T. Volkel, et al., *Biochimica et Biophysica Acta*, 1663:158-166 (2004). Junction membrane protein vascular endothelial (VE)-cadherin has been shown to bind to endothelial cells and down regulate apoptosis of the endothelial cells. R. Spagnuolo, et al., *Blood*, 103:3005-3012 (2004).

In a particular embodiment, the EDC-binding agent can be the active fragment of osteopontin, (Asp-Val-Asp-Val-Pro-Asp-Gly-Asp-Ser-Leu-Ala-Try-Gly). Other EDC-binding agents include, but are not limited to, EPC (epithelial cell) antibodies, RGD peptide sequences, RGD mimetics, and combinations thereof.

In further embodiments, the prohealing drug or agent can be a substance or agent that attracts and binds endothelial progenitor cells. Representative substances or agents that attract and bind endothelial progenitor cells include antibodies such as CD-34, CD-133 and vegf type 2 receptor. An agent that attracts and binds endothelial progenitor cells can include a polymer having nitric oxide donor groups.

The foregoing biologically active agents are listed by way of example and are not meant to be limiting. Other biologically active agents that are currently available or that may be developed in the future are equally applicable.

In a more specific embodiment, optionally in combination with one or more other embodiments described herein, the implantable device of the invention comprises at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, progenitor cell-capturing antibodies, prohealing drugs, pro-drugs thereof, co-drugs thereof, and a combination thereof. In a particular embodiment, the bioactive agent is everolimus. In another specific embodiment, the bioactive agent is clobetasol.

An alternative class of drugs would be p-para-α-agonists for increased lipid transportation, examples include fenofibrate.

In some embodiments, optionally in combination with one or more other embodiments described herein, the at least one biologically active agent specifically cannot be one or more of any of the bioactive drugs or agents described herein.

Coating Construct

According to some embodiments of the invention, optionally in combination with one or more other embodiments described herein, a coating disposed over an implantable device (e.g., a stent) can include a semi-crystalline polymer described herein in a layer according to any design of a coating. The coating can be a multi-layer structure that includes at least one reservoir layer, which is layer (2) described below, and can include any of the following (1), (3), (4) and (5) layers or combination thereof:

(1) a primer layer; (optional)
(2) a reservoir layer (also referred to "matrix layer" or "drug matrix"), which can be a drug-polymer layer including at least one polymer (drug-polymer layer) or, alternatively, a polymer-free drug layer;
(3) a release control layer (also referred to as a "rate-limiting layer") (optional);
(4) a topcoat layer; and/or (optional);
(5) a finishing coat layer. (optional).

In some embodiments, a coating of the invention can include two or more reservoir layers described above, each of which can include a bioactive agent described herein.

Each layer of a stent coating can be disposed over the implantable device (e.g., a stent) by dissolving the semi-crystalline polymer, optionally with one or more other polymers, in a solvent, or a mixture of solvents, and disposing the resulting coating solution over the stent by spraying or immersing the stent in the solution. After the solution has been disposed over the stent, the coating is dried by allowing the solvent to evaporate. The process of drying can be accelerated if the drying is conducted at an elevated temperature. The complete stent coating can be optionally annealed at a temperature between about 40° C. and about 150° C., e.g., 80° C., for a period of time between about 5 minutes and about 60 minutes, if desired, to allow for crystallization of the polymer coating, and/or to improve the thermodynamic stability of the coating.

To incorporate a bioactive agent (e.g., a drug) into the reservoir layer, the drug can be combined with the polymer solution that is disposed over the implantable device as described above. Alternatively, if it is desirable a polymer-free reservoir can be made. To fabricate a polymer-free reservoir, the drug can be dissolved in a suitable solvent or mixture of solvents, and the resulting drug solution can be disposed over the implantable device (e.g., stent) by spraying or immersing the stent in the drug-containing solution.

Instead of introducing a drug via a solution, the drug can be introduced as a colloid system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the solvent to form the solvent phase of the suspension, as well as the quantity of the drug to be dispersed in the solvent phase. Optionally, a surfactant can be added to stabilize the suspension. The suspension can be mixed with a polymer solution and the mixture can be disposed over the stent as described above. Alternatively, the drug suspension can be disposed over the stent without being mixed with the polymer solution.

The drug-polymer layer can be applied directly or indirectly over at least a portion of the stent surface to serve as a reservoir for at least one bioactive agent (e.g., drug) that is incorporated into the reservoir layer. The optional primer layer can be applied between the stent and the reservoir to improve the adhesion of the drug-polymer layer to the stent. The optional topcoat layer can be applied over at least a portion of the reservoir layer and serves as a rate-limiting membrane that helps to control the rate of release of the drug. In one embodiment, the topcoat layer can be essentially free from any bioactive agents or drugs. If the topcoat layer is used, the optional finishing coat layer can be applied over at least a portion of the topcoat layer for further control of the drug-release rate and for improving the biocompatibility of the coating. Without the topcoat layer, the finishing coat layer can be deposited directly on the reservoir layer.

Sterilization of a coated medical device generally involves a process for inactivation of micropathogens. Such processes are well known in the art. A few examples are e-beam, ETO sterilization, and irradiation. Most, if not all, of these processes can involve an elevated temperature. For example, ETO sterilization of a coated stent generally involves heating above 50° C. at humidity levels reaching up to 100% for periods of a few hours up to 24 hours. A typical EtO cycle would have the temperature in the enclosed chamber to reach as high as above 50° C. within the first 3-4 hours then and fluctuate between 40° C. to 50° C. for 17-18 hours while the humidity would reach the peak at 100% and maintain above 80% during the fluctuation time of the cycle.

The process of the release of a drug from a coating having both topcoat and finishing coat layers includes at least three steps. First, the drug is absorbed by the polymer of the topcoat layer at the drug-polymer layer/topcoat layer interface. Next, the drug diffuses through the topcoat layer using the void volume between the macromolecules of the topcoat layer polymer as pathways for migration. Next, the drug arrives at the topcoat layer/finishing layer interface. Finally, the drug diffuses through the finishing coat layer in a similar fashion, arrives at the outer surface of the finishing coat layer, and desorbs from the outer surface. At this point, the drug is released into the blood vessel or surrounding tissue. Consequently, a combination of the topcoat and finishing coat layers, if used, can serve as a rate-limiting barrier. The drug can be released by virtue of the degradation, dissolution, and/or erosion of the layer(s) forming the coating, or via migration of the drug through the semi-crystalline polymeric layer(s) into a blood vessel or tissue.

In one embodiment, any or all of the layers of the stent coating can be made of a semi-crystalline polymer described herein, optionally having the properties of being biologically degradable/erodable/absorbable/resorbable, non-degradable/biostable polymer, or a combination thereof. In another embodiment, the outermost layer of the coating can be limited to a semi-crystalline polymer as defined above.

To illustrate in more detail, in a stent coating having all four layers described above (i.e., the primer, the reservoir layer, the topcoat layer and the finishing coat layer), the outermost layer is the finishing coat layer, which can be made of a semi-crystalline polymer described herein and optionally having the properties of being biodegradable or, biostable, or being mixed with an amorphous polymer. The remaining layers (i.e., the primer, the reservoir layer and the topcoat layer) optionally having the properties of being biodegradable or, biostable, or being mixed with an amorphous polymer. The polymer(s) in a particular layer may be the same as or different than those in any of the other layers, as long as the layer on the outside of another bioabsorbable should preferably also be bioabsorbable and degrade at a similar or faster relative to the inner layer. As another illustration, the coating can include a single matrix layer comprising a polymer described herein and a drug.

If a finishing coat layer is not used, the topcoat layer can be the outermost layer and should be made of a semi-crystalline polymer described herein and optionally having the properties of being biodegradable or, biostable, or being mixed with an amorphous polymer. In this case, the remaining layers (i.e., the primer and the reservoir layer) optionally can also be fabricated of a semi-crystalline polymer described herein and optionally having the properties of being biodegradable or, biostable, or being mixed with an amorphous polymer The polymer(s) in a particular layer may be the same as or different than those in any of the other layers, as long as the outside of another bioabsorbable should preferably also be bioabsorbable and degrade at a similar or faster relative to the inner layer.

If neither a finishing coat layer nor a topcoat layer is used, the stent coating could have only two layers—the primer and the reservoir. In such a case, the reservoir is the outermost layer of the stent coating and should be made of a semi-crystalline polymer described herein and optionally having the properties of being biodegradable or, biostable, or being mixed with an amorphous polymer. The primer optionally can also be fabricated of a semi-crystalline polymer described herein and optionally one or more biodegradable polymer(s), biostable polymer(s), or a combination thereof. The two layers may be made from the same or different polymers, as long as the layer on the outside of another bioabsorbable should preferably also be bioabsorbable and degrade at a similar or faster relative to the inner layer.

Any layer of a coating can contain any amount of a semi-crystalline polymer described herein and optionally having the properties of being biodegradable or, biostable, or being mixed with an amorphous polymer. Non-limiting examples of bioabsorbable polymers and biocompatible polymers include poly(N-vinyl pyrrolidone); polydioxanone; polyorthoesters; polyanhydrides; poly(glycolic acid); poly(glycolic acid-co-trimethylene carbonate); polyphosphoesters; polyphosphoester urethanes; poly(amino acids); poly(trimethylene carbonate); poly(iminocarbonates); co-poly(etheresters); polyalkylene oxalates; polyphosphazenes; biomolecules, e.g., fibrin, fibrinogen, cellulose, cellophane, starch, collagen, hyaluronic acid, and derivatives thereof (e.g., cellulose acetate, cellulose butyrate, cellulose acetate butyrate, cellulose nitrate, cellulose propionate, cellulose ethers, and carboxymethyl cellulose), polyurethane, polyesters, polycarbonates, polyurethanes, poly(L-lactic acid-co-caprolactone) (PLLA-CL), poly(D-lactic acid-co-caprolactone) (PDLA-CL), poly(DL-lactic acid-co-caprolactone) (PDLLA-CL), poly(D-lactic acid-glycolic acid (PDLA-GA), poly(L-lactic acid-glycolic acid (PLLA-GA), poly(DL-lactic acid-glycolic acid (PDLLA-GA), poly(D-lactic acid-co-glycolide-co-caprolactone) (PDLA-GA-CL), poly(L-lactic acid-co-glycolide-co-caprolactone) (PLLA-GA-CL), poly(DL-lactic acid-co-glycolide-co-caprolactone) (PDLLA-GA-CL), poly (L-lactic acid-co-caprolactone) (PLLA-CL), poly(D-lactic acid-co-caprolactone) (PDLA-CL), poly(DL-lactic acid-co-caprolactone) (PDLLA-CL), poly(glycolide-co-caprolactone) (PGA-CL), or any copolymers thereof.

Any layer of a stent coating can also contain any amount of a non-degradable polymer, or a blend of more than one such polymer as long as it is not mixed with a bioabsorbable polymer or any layer underneath the non-degradable layer comprise a bioabsorbable polymer. Non-limiting examples of non-degradable polymers include methylmethacrylate, ethylmethacrylate, butylmethacrylate, 2-ethylhexylmethacrylate, laurylmethacrylate, hydroxyl ethyl methacrylate, polyethylene glycol (PEG) acrylate, PEG methacrylate, 2-methacryloyloxyethylphosphorylcholine (MPC) and n-vinyl pyrrolidone, methacrylic acid, acrylic acid, hydroxypropyl methacrylate, hydroxypropylmethacrylamide, 3-trimethylsilylpropyl methacrylate, and copolymers thereof.

Method of Fabricating Implantable Device

Other embodiments of the invention, optionally in combination with one or more other embodiments described herein, are drawn to a method of fabricating an implantable device. In one embodiment, the method comprises forming the implantable device of a material containing a biodegradable or biostable polymer or copolymer.

Under the method, a portion of the implantable device or the whole device itself can be formed of the material containing a biodegradable or biostable polymer or copolymer. The method can deposit a coating having a range of thickness over an implantable device. In certain embodiments, the method deposits over at least a portion of the implantable device a coating that has a thickness of $\leq$about 30 micron, or $\leq$about 20 micron, or $\leq$about 10 micron, or $\leq$about 5 micron.

In certain embodiments, the method is used to fabricate an implantable device selected from stents, grafts, stent-grafts, catheters, leads and electrodes, clips, shunts, closure devices, valves, and particles. In a specific embodiment, the method is used to fabricate a stent.

In some embodiments, to form an implantable device formed from a polymer, a polymer or copolymer optionally including at least one bioactive agent described herein can be formed into a polymer construct, such as a tube or sheet that can be rolled or bonded to form a construct such as a tube. An implantable device can then be fabricated from the construct. For example, a stent can be fabricated from a tube by laser machining a pattern into the tube. In another embodiment, a polymer construct can be formed from the polymeric material of the invention using an injection-molding apparatus.

Non-limiting examples of polymers, which may or may not be the semi-crystalline polymers defined above, that can be used to fabricate an implantable device include poly(N-acetylglucosamine) (Chitin), Chitosan, poly(hydroxyvalerate), poly(lactide-co-glycolide), poly(hydroxybutyrate), poly (hydroxybutyrate-co-valerate), polyorthoester, polyanhydride, poly (L-lactic acid-co-caprolactone) (PLLA-CL), poly(D-lactic acid-co-caprolactone) (PDLA-CL), poly (DL-lactic acid-co-caprolactone) (PDLLA-CL), poly(D-lactic acid-glycolic acid (PDLA-GA), poly(L-lactic acid-glycolic acid (PLLA-GA), poly(DL-lactic acid-glycolic acid (PDLLA-GA), poly(D-lactic acid-co-glycolide-co-caprolactone) (PDLA-GA-CL), poly(L-lactic acid-co-glycolide-co-caprolactone) (PLLA-GA-CL), poly(DL-lactic acid-co-glycolide-co-caprolactone) (PDLLA-GA-CL), poly(L-lactic acid-co-caprolactone) (PLLA-CL), poly(D-lactic acid-co-caprolactone) (PDLA-CL), poly(DL-lactic acid-co-caprolactone) (PDLLA-CL), poly(glycolide-co-caprolactone) (PGA-CL), poly(thioesters), poly(trimethylene carbonate), polyethylene amide, polyethylene acrylate, poly(glycolic acid-co-trimethylene carbonate), co-poly(ether-esters) (e.g., PEO/PLA), polyphosphazenes, biomolecules (e.g., fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (e.g., polyvinyl chloride), polyvinyl ethers (e.g., polyvinyl methyl ether), polyvinylidene halides (e.g., polyvinylidene chloride), polyacrylonitrile, polyvinyl ketones, polyvinyl aromatics (e.g., polystyrene), polyvinyl esters (e.g., polyvinyl acetate), acrylonitrile-styrene copolymers, ABS resins, polyamides (e.g., Nylon 66 and polycaprolactam), polycarbonates, polyoxymethylenes, polyimides, polyethers, polyurethanes, rayon, rayon-triacetate, cellulose and derivates thereof (e.g., cellulose acetate, cellulose butyrate, cellulose acetate butyrate, cellophane, cellulose nitrate, cellulose propionate, cellulose ethers, and carboxymethyl cellulose), and copolymers thereof.

Additional representative examples of polymers that may be suited for fabricating an implantable device include ethylene vinyl alcohol copolymer (commonly known by the generic name EVOH or by the trade name EVAL), poly(butyl methacrylate), poly(vinylidene fluoride-co-hexafluoropropylene) (e.g., SOLEF 21508, available from Solvay Solexis PVDF of Thorofare, N.J.), polyvinylidene fluoride (otherwise known as KYNAR, available from ATOFINA Chemicals of Philadelphia, Pa.), poly(tetrafluoroethylene-co-hexafluoropropylene-co-vinylidene fluoride), ethylene-vinyl acetate copolymers, and polyethylene glycol.

Method of Treating or Preventing Disorders

An implantable device according to the present invention can be used to treat, prevent or diagnose various conditions or disorders. Examples of such conditions or disorders include, but are not limited to, atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. A portion of the implantable device or the whole device itself can be formed of the material, as described herein. For example, the material can be a coating disposed over at least a portion of the device.

In certain embodiments, optionally in combination with one or more other embodiments described herein, the inventive method treats, prevents or diagnoses a condition or disorder selected from atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. In a particular embodiment, the condition or disorder is atherosclerosis, thrombosis, restenosis or vulnerable plaque.

In one embodiment of the method, optionally in combination with one or more other embodiments described herein, the implantable device is formed of a material or includes a coating containing at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, progenitor cell-capturing antibodies, prohealing drugs, fenofibrate, prodrugs thereof, co-drugs thereof, and a combination thereof.

In certain embodiments, optionally in combination with one or more other embodiments described herein, the implantable device used in the method is selected from stents, grafts, stent-grafts, catheters, leads and electrodes, clips, shunts, closure devices, valves, and particles. In a specific embodiment, the implantable device is a stent.

Example 1

Coatings comprising a PEG-PLGA IPN with a weight average molecular weight (Mw) of about 34 KDa were formed on Vision stents (3 mm×12 mm, available from Abbott Vascular, Santa Clara, Calif.) with formulations described below. The coatings showed acceptable coating integrity after E-beam (Scanning Electron Microscope (SEM) images not shown) and a reasonable controlled release of the everolimus (Table 1).
Sample formulation:
drug:polymer (D:P)=1:3;
solvent: 100% acetone;
dose: 100 μg/cm$^2$ dose;
sterilization: E-beam

TABLE 1

| | Total Content and release rate results | | |
| --- | --- | --- | --- |
| Sample | Lot# | Total Drug Content (%), n = 3 | release rate (RR) day 1 (5), n = 3 | RR day 3 (%), n = 3 |
| PEG-IPN with D:P = 1:3 | 081107 | 73.8 ± 5.3 | 68.1 ± 4.7 | 81.1 ± 1.3 |

Example 2

Figure 1B:
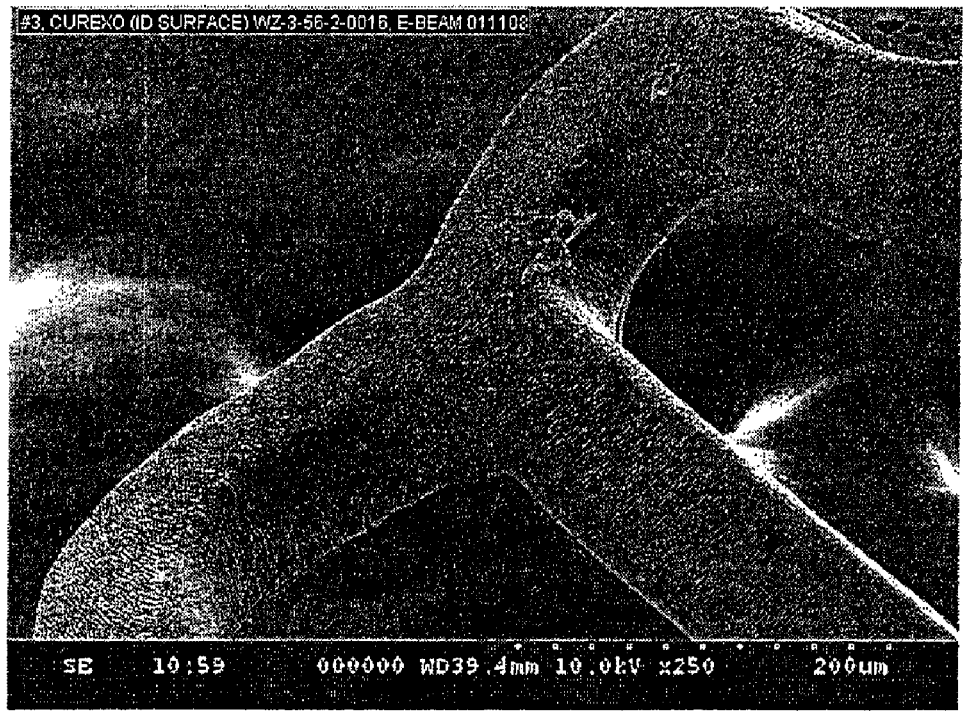
Figure 1C:
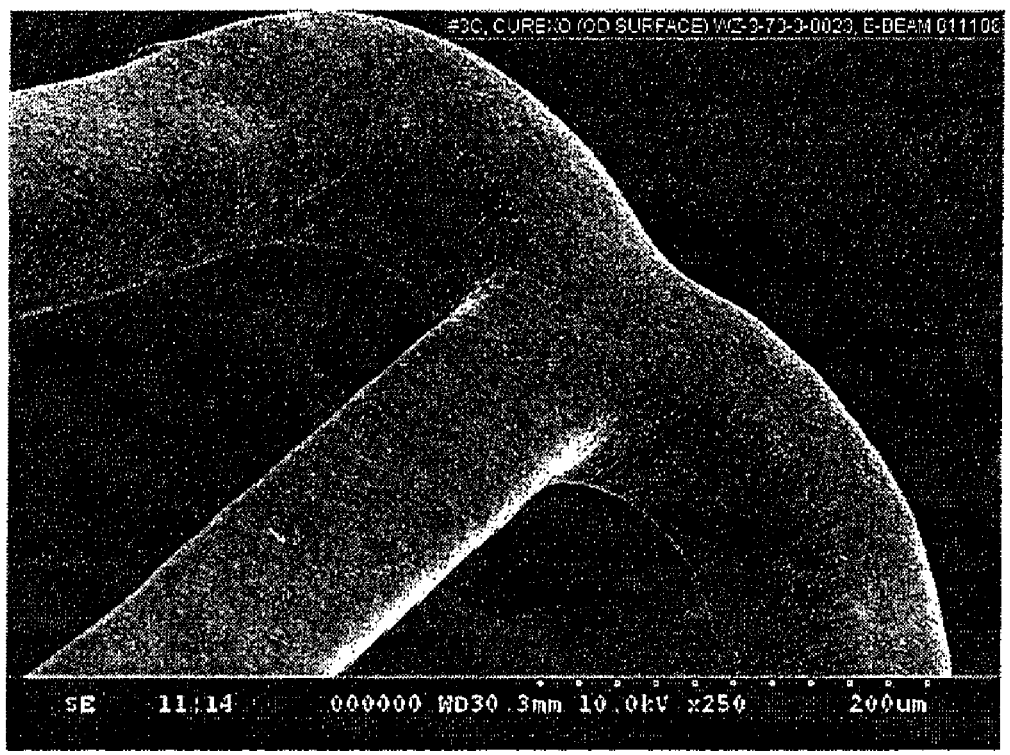
Figure 1D:
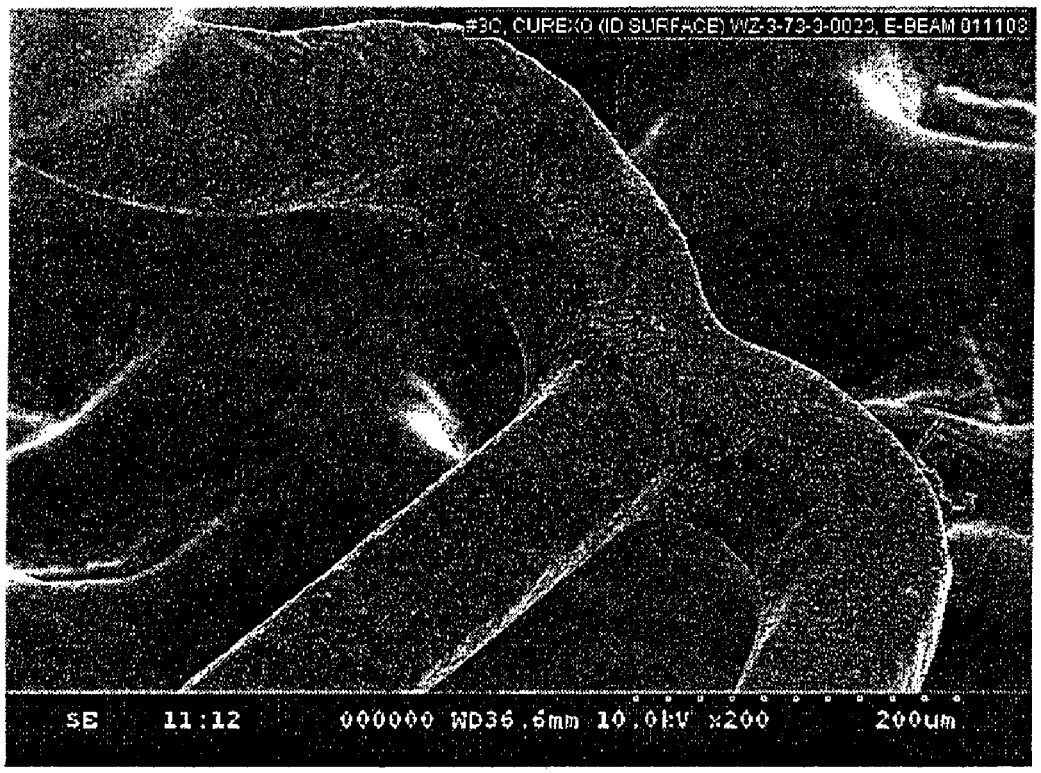
Figure 1E:
Figure 1F:
Figure 2:
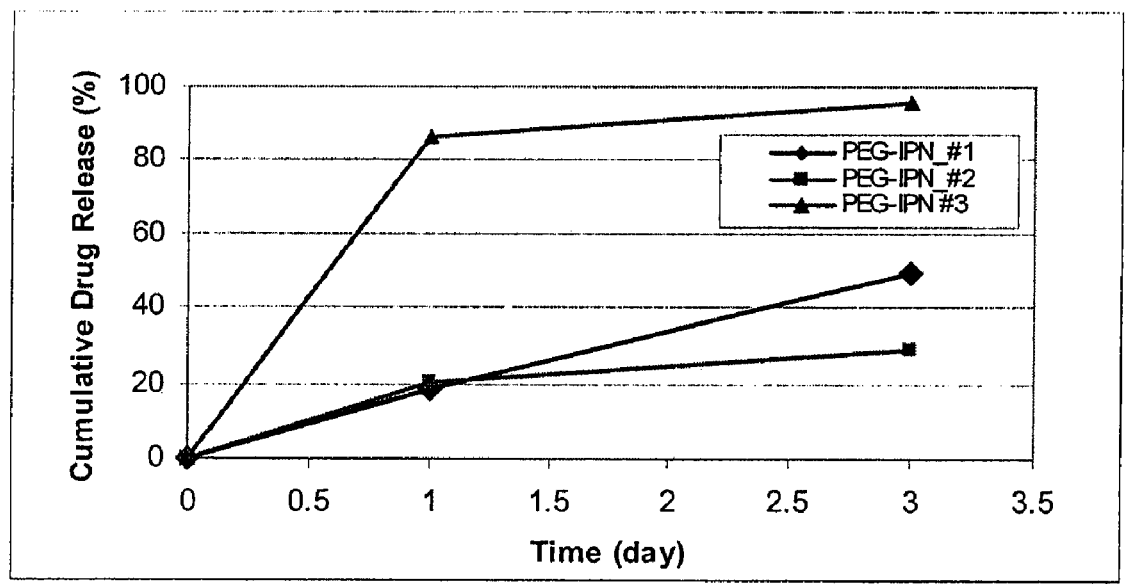
FIG. 2 shows release rate profiles of everolimus from coatings formed from various PEG-PLGA IPN compositions.

Coatings comprising various compositions of PEG in PEG-PLGA IPN with a weight average molecular weight (Mw) of about 34 KDa were formed on Vision stents (3 mm×12 mm, available from Abbott Vascular, Santa Clara, Calif.) with formulations described below. The coatings showed acceptable coating integrity after E-beam (FIGS. 1A-1F) and release rate that is dependent on the composition of the PEG in the IPN (FIG. 2).
Sample formulation:
drug:polymer (D:P)=1:2;
solvent: 100% acetone;
dose: 100 μg/cm$^2$ dose;
sterilization: E-beam FIGS. 1A-1B: Coating Integrity of PEG-IPN #1
1C-1D: Coating integrity of PEG-IPN #2
1E-1F: Coating integrity of PEG-IPN #3

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for fabricating a coating for an implantable medical device, the method comprising forming a coating on the implantable medical device, the coating comprising an interpenetrating network (IPN) or semi-IPN, wherein the IPN or semi-IPN comprises poly(ethylene glycol) (PEG) and an aliphatic polyester copolymer; and
wherein forming the coating comprises crosslinking the PEG and the aliphatic polyester copolymer.

2. The method of claim 1, wherein forming the coating comprises crosslinking the PEG and the aliphatic polyester copolymer with a bifunctional or multifunctional crosslinking agent.

3. The method of claim 1, wherein the aliphatic polyester copolymer comprises D,L-lactide or L-lactide.

4. The method of claim 1, wherein the aliphatic polyester copolymer comprises glycolide (GA).

5. The method of claim 1, wherein the aliphatic polyester copolymer comprises poly(lactide-co-glycolide-co-caprolactone) (PLGACL), poly(lactide-co-glycolide) (PLGA), or poly(butylene succinate).

6. The method of claim 1, wherein the IPN or semi-IPN comprises from about 1% to about 40% PEG by mass of the IPN or semi-IPN.

7. The method of claim 1, wherein the IPN or semi-IPN comprises from about 2% to about 25% PEG by mass of the IPN or semi-IPN.

8. The method of claim 1, wherein the IPN or semi-IPN comprises from about 2% to about 10% PEG by mass of the IPN or semi-IPN.

9. The method of claim 1, wherein the aliphatic polyester copolymer comprises lactide and glycolide in a molar ratio of lactide to glycolide ranging from about 50:50 to about 90:10.

10. The method of claim 1, wherein the aliphatic polyester copolymer comprises lactide and glycolide in a molar ratio of lactide to glycolide of about 75:25.

11. The method of claim 1, wherein coating further comprises a bioactive agent.

12. The method of claim 1, wherein coating further comprises a bioactive agent, and wherein the bioactive agent and the IPN or semi-IPN are in a weight ratio of the bioactive agent to the IPN or semi-IPN of about 1:1 to about 1:5.

13. The method of claim 1, wherein the coating further comprises a bioactive agent selected from the group consisting of paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, dexamethasone acetate, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), zotarolimus, Biolimus A9 (Biosensors International, Singapore), AP23572 (Ariad Pharmaceuticals), γ-hiridun, clobetasol, pimecrolimus, imatinib mesylate, midostaurin, feno fibrate, prodrugs thereof, co-drugs thereof, and combinations thereof.

14. The method of claim 1, wherein the implantable medical device is a stent.

15. The method of claim 1, wherein the IPN is constructed using PEG-co-poly(butylene succinate) and PLGA, or is constructed using PEG-co-PLGA and PLGA.

* * * * *